US011112414B2

(12) United States Patent
Rouet et al.

(10) Patent No.: US 11,112,414 B2
(45) Date of Patent: Sep. 7, 2021

(54) BIOMARKER OF REHOSPITALIZATION AFTER HEART FAILURE

(71) Applicants: INSERM (Institut National de la Sante et de la Recherche Medicale), Paris (FR); Universite Paul Sabatier Toulouse III, Toulouse (FR); Centre Hospitalier Universitaire de Toulouse, Toulouse (FR)

(72) Inventors: Philippe Rouet, Toulouse (FR); Fatima Smith-Rouet, Toulouse (FR); Franck Desmoulin, Toulouse (FR); Michel Galinier, Toulouse (FR)

(73) Assignees: INSERM (INSTITUTE NATIONAL DE LAS SANTE ET DE LA RECHERCHE MEDICALE), Paris (FR); UNIVERSITE PAUL SABATIER TOULOUSE III, Toulouse (FR); CENTRE HOSPITALIER UNIVEERSITAIRE DE TOULOUSE, Toulouse (FR)

( * ) Notice: Subject to any disclaimer, the term of this patent is extended or adjusted under 35 U.S.C. 154(b) by 194 days.

(21) Appl. No.: 14/895,076

(22) PCT Filed: Jun. 6, 2014

(86) PCT No.: PCT/EP2014/061819
§ 371 (c)(1),
(2) Date: Dec. 1, 2015

(87) PCT Pub. No.: WO2014/195456
PCT Pub. Date: Dec. 11, 2014

(65) Prior Publication Data
US 2016/0123995 A1    May 5, 2016

(30) Foreign Application Priority Data

Jun. 6, 2013  (EP) ..................... 13305760

(51) Int. Cl.
*G01N 33/53* (2006.01)
*G01N 33/68* (2006.01)
*G01N 33/74* (2006.01)

(52) U.S. Cl.
CPC ......... *G01N 33/6893* (2013.01); *G01N 33/74* (2013.01); *G01N 2333/4704* (2013.01); *G01N 2333/4745* (2013.01); *G01N 2800/325* (2013.01); *G01N 2800/56* (2013.01)

(58) Field of Classification Search
CPC .............. G01N 33/6893; G01N 33/74; G01N 2333/4704; G01N 2333/4745; G01N 2800/325; G01N 2800/56
See application file for complete search history.

(56) References Cited

U.S. PATENT DOCUMENTS

| 2006/0172429 | A1 | 8/2006 | Nilsson et al. | |
|---|---|---|---|---|
| 2014/0206632 | A1* | 7/2014 | Todd | G01N 33/6869 514/26 |
| 2015/0119269 | A1* | 4/2015 | McPherson | G01N 33/6896 506/9 |

FOREIGN PATENT DOCUMENTS

| JP | 2010517023 A | 5/2010 |
|---|---|---|
| WO | 2008/005469 A2 | 1/2008 |
| WO | 2008/089994 A1 | 7/2008 |
| WO | 2014/023820 A1 | 2/2014 |

OTHER PUBLICATIONS

Mischak et al., Comprehensive human urine standards for comparability and standardization in clinical proteome analysis, Proteomics Coin Appl. Apr. 2010; 4(4), pp. 464-478.*
Mehani., Correlation between changes in diastolic dysfunction and health-related quality of life after cardiac rehabilitation program in dilated cardiomyopathy, Journal of Advanced Research, 2013, 4, pp. 189-200, available online Aug. 3, 2012.*
Satomura et al., Congestive heart failure in the elderly: Comparison between reduced ejection fraction and preserved ejection fraction, Journal of Cardiology 2012, 59, pp. 215-219. (Year: 2012).*
Paulus et al., How to diagnose diastolic heart failure: a consensus statement on the diagnosis of heart failure with normal left ventricular ejection fraction, European Heart Journal, 2007, 28, pp. 2539-2550. (Year: 2007).*
Narayanan et al; "IGF binding protein-2 is associated with all-cause and cardiovascular mortality in type 2 diabetes"; retrieved from the internet: URL:http://www.endocrine-abstracts.org/ea/0031/ea0031p139.htm, retrieved on 2013-19-25, the entire document.

(Continued)

*Primary Examiner* — Gary Counts
(74) *Attorney, Agent, or Firm* — W&C IP

(57) ABSTRACT

The invention is a method for treating a heart failure patient with the steps of measuring the concentration of IGFBP2 in a blood, plasma or urine sample obtained from the heart failure patient and comparing the patient's IGFBP2 level to a threshold value derived from IGFBP2 measured in samples taken from a group of patients with heart failure selected from the group consisting of stage I, stage stage III and stage IV heart failure, according to New York Heart Association (NYHA) classification system. A patient with an IGFBP2 level that exceeds the threshold value is admitted or readmitted to a hospital and treated with at least one treatment selected from the group consisting of administration of a beta-blocker, an angiotensin-converting enzyme inhibitor, an angiotensin receptor blocker, an aldosterone antagonist, an implantable cardiac defibrillator, a cardiac resynchronization therapy, an implantable left ventricular assist device and a heart transplant.

13 Claims, 4 Drawing Sheets

(56) References Cited

OTHER PUBLICATIONS

Figure 1:
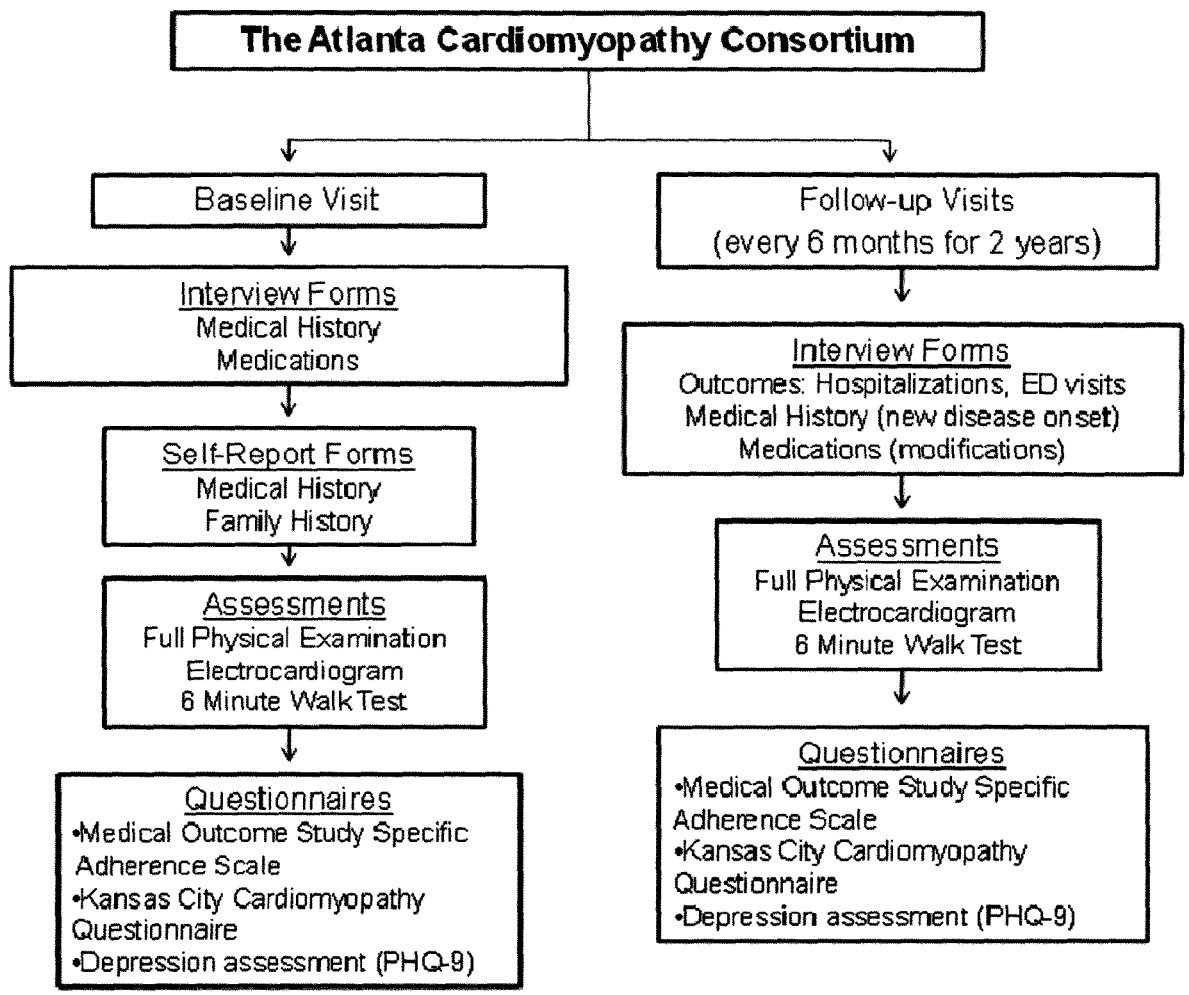

Hassfeld et al.; "Insulin-like growth factor-binding proteins 2 and 3 are independent predictors of a poor prognosis in patients with dilated cardiomyopathy", Heart, vol. 93, No. 3, 2007-03-01, pp. 359-360.

Motiwala et al.; "Using Biomarkers to "Guide" Heart Failure Management"; Cardiology in Review, vol. 21, No. 3, Jan. 1, 2013, pp. 127-134.

Philbin et al; "Prediction of hospital readmission for heart failure: development of a simple risk score based on administrative data"; Journal of the American College of Cardiology, vol. 33, No. 6, May 1, 1999, pp. 1560-1566.

Janszky et al: "Insulin-like growth factor binding protein-1 is long-term predictor of heart failure in survivors of a first acute myocardial infarction and population controls", International Journal of Cardiology, vol. 138, pp. 50-55, 2010.

\* cited by examiner

*Kruskall Wallis test P=0.0015, post hoc comparison with Q1 and Q2 p<0.05

$ Patient mean annual rate of hospitalization for All-cause

| Quartiles | Q1 | Q2 | Q3 | Q4 | |
|---|---|---|---|---|---|
| N | 77 | 76 | 77 | 76 | |
| Median (ng/ml) | 51.5 | 126.9 | 213.9 | 391.8 | |
| (95% CI) | (44.7-55.8) | (111.6-136.4) | (205.5-226.0) | (356.8-445.4) | |
| Lower limit (ng/ml) | 1.8 | 76.8 | 174.0 | 278.4 | |
| Higher limit (ng/ml) | 75.9 | 171.0 | 274.0 | 1203.6 | |
| All-cause Hospiatlization rate | Q1 | Q2 | Q3 | Q4 | p for trend |
| Median | 0.48 | 0.49 | 0.77 | 1.07 | 0.003 |
| (95% CI) | (0.25-0.66) | (0.25-0.65) | (0.51-0.95) | (0.48-1.70) | |

*Kruskall Wallis test P=0.0018, post hoc comparison with Q1 and Q2 p<0.05

$ Patient mean annual rate of hospitalization for heart failure cause

| Quartiles | Q1 | Q2 | Q3 | Q4 | |
|---|---|---|---|---|---|
| N | 77 | 76 | 77 | 76 | |
| Median (ng/ml) | 51.5 | 126.9 | 213.9 | 391.8 | |
| (95% CI) | (44.7-55.8) | (111.6 - 136.4) | (205.5 - 226.0) | (356.8 - 445.4) | |
| Lower limit (ng/ml) | 1.8 | 76.8 | 174.0 | 278.4 | |
| Higher limit (ng/ml) | 75.9 | 171.0 | 274.0 | 1203.6 | |
| Heart failure Hospiatlization rate | Q1 | Q2 | Q3 | Q4 | p for trend |
| 75th Percentile | 0 | 0 | 0.48 | 1.42 | 0.0003 |

BIOMARKER OF REHOSPITALIZATION AFTER HEART FAILURE

FIELD OF THE INVENTION

The invention relates to a method for establishing if a heart failure patient is susceptible to be hospitalized and/or rehospitalized, wherein said method comprises measuring the concentration of IGFBP2 in a sample obtained from said heart failure patient.

BACKGROUND OF THE INVENTION

Prevalence of heart failure (HF) is growing because of the ageing and the cardiovascular risk factors in general population [Delahaye, F. et al., 2001]. The HF diagnosis remains too often complicated because of atypical presentation and the need to specialized care access. To help clinicians diagnose heart failure, blood HF biomarkers have been proposed, such as the natriuretic peptides (NP). However, NP have limitations which sustains a need for more specific and more acurate biomarkers that would allow for facilitated large scale HF screenings. In addition, 30% of the patients admitted to emergency care for acute dyspnea have a brain natriuretic peptides (BNP) concentration in a <<gray zone>> that does not allow for diagnosis. In these cases, HF diagnosis will require costly and time consuming examinations. However, it is recognized that a rapid diagnosis and early medical care of the patient have a positive impact on the patient's health and also lower the cost of the treatment.

Hospitalized heart failure patient's safe discharge is a very important challenge. To avoid a vital risk for the patient, it is essential to evaluate carefully the patient's clinical status through clinical examination but also with the support of objective biological parameters. Moreover, a rehospitalization due to optimistic estimation of the patient's prognostic can cause important financial issues to the Hospital in the United states through penalty determined by a calculation of an excess readmission ratio for heart failure (Hospital Readmission Reduction Program of the social security: cms.gov/Medicare/Medicare-Fee-for-Service Payment/AcutelnpatientPPS/Readmissions-Reduction-Program.html). Thus, it is of interest to have an objective biological biomarker of rehospitalization after heart failure.

SUMMARY OF THE INVENTION

The inventors have launched a prospective study with patients with Heart Failure (HF) from three university-affiliated hospitals in the greater metropolitan Atlanta area. Univariate analysis revealed an association of IGFBP2 with readmission of patients for heart failure.

Thus, the invention relates to a method for establishing if a heart failure patient is susceptible to be hospitalized and/or rehospitalized, wherein said method comprises measuring the concentration of IGFBP2 in a sample obtained from said heart failure patient.

DETAILED DESCRIPTION OF THE INVENTION

Method for Estimation of Hospitalization and Rehospitalisation Risk

The invention relates to a method for establishing if a heart failure patient is susceptible to be hospitalized and/or rehospitalized, wherein said method comprises measuring the concentration of IGFBP2 in a sample obtained from said heart failure patient.

In one embodiment, the invention relates to a method for establishing if a heart failure patient is susceptible to be hospitalized (rate of hospitalization) and/or rehospitalized (rate of rehospitalisation), wherein said method comprises measuring the concentration of IGFBP2 in a sample obtained from said heart failure patient.

In a particular embodiment, said method further comprises the steps of:
(i) measuring the concentration of IGFBP2 in a sample obtained from said heart failure patient,
(ii) comparing the concentration of IGFBP2 measured in step (i) to a threshold value derived from the concentration of IGFBP2 in samples from patients who are at particular stages of heart failure and/or to a threshold value derived from the concentration of IGFBP2 in samples from healthy patients.

In one embodiment, the threshold value corresponds to the second quartile (median) concentration in samples from patients with a chronic heart failure. This threshold value is between the median value of patient who were not hospitalized and the median value of patient who were hospitalized or rehospitalized.

The invention also relates to a method for establishing if a heart failure patient is susceptible to be hospitalized or rehospitalized comprising the steps consisting of i) determining the concentration of IGFBP2 in a sample obtained from said patient; and ii) comparing said concentration to the threshold value.

As used herein, the term "a heart failure patient" denotes a patient who suffers of heart failure and who is hospitalized or who has been hospitalized for a heart failure at any stage. The term "a heart failure patient" also denotes a patient who has been hospitalized for heart failure in the past.

As used herein, the term "rehospitalized" denotes a patient who has been hospitalized for a heart failure and who is again hospitalized. In this context the patient is hospitalized again for the same disease. In other word, the term "rehospitalized" denotes further hospithalization due to heart failure.

In one embodiment, the heart failure may be an asymptomatic heart failure, a chronic heart failure or an acute heart failure.

Typically, the sample according to the invention may be a blood, plasma, serum, lymph or urine sample. In a particular embodiment, said sample is blood or plasma.

As used herein, the term "IGFBP2" for "Insulin-like Growth Factor-Binding Protein 2" denotes a protein which serves as a carrier protein for Insulin-like growth factor 1 (IGF I) or Insulin-like growth factor 2 (IGF II). As used herein, the term "IGFBP2" denotes also fragments of IGFBP2. As used herein, the term "fragments of IGFBP2" denotes shorter peptides becoming from chemical or biochemical hydrolysis of IGFBP2.

As used herein, the term "heart failure" denotes inability of the heart to supply sufficient blood flow to meet the body's needs and this pathology is well-described in medicine practice. This term encompasses chronic heart failure, acute heart failure, myocardial infarction, unstable angina, diastolic dysfunction, systolic dysfunction and diabetic cardiomyopathy.

As used herein, the term diabetic cardiomyopathy is a form of heart failure which leads to inability of the heart to circulate blood through the body.

As used herein, the term "chronic heart failure" denotes a long term situation, usually with stable treated symptomatology.

As used herein, the term "acute heart failure" denotes to sudden onset heart failure, as well as acute "exacerbated" or "decompensated" heart failure, referring to episodes in which a patient with known chronic heart failure or devoid of chronic heart failure abruptly develops worsening symptoms and requires hospitalization. Common complications due to acute heart failure include, but are not limited to, dyspnea due to pulmonary congestion or cardiogenic shock due to low cardiac output, easy fatigueability (exercise intolerance), peripheral edema, anasarca (pronounced generalized edema), hypotension, syncope, oliguria or anuria, hyperkalemia.

A patient with a heart failure is classified according to an international gradation namely the New York Heart Association (NYHA) functional classification. Functional classification of heart failure is generally done by the New York Heart Association Functional Classification (Criteria Committee, New York Heart Association. Diseases of the heart and blood vessels). Nomenclature and criteria for diagnosis, 6th ed. Boston: Little, Brown and co, 1964; 114). This classification stages the severity of heart failure into 4 classes (I-IV).

A patient with cardiac disease but resulting in no limitation of physical activity is classified as a NYHA class I. Ordinary physical activity does not cause undue fatigue, palpitation, dyspnea or anginal pain. A asymptomatic patient is classified as a NYHA class I.

A patient with cardiac disease resulting in slight limitation of physical activity is classified as a NYHA class II. Ordinary physical activity results in fatigue, palpitation, dyspnea or anginal pain. They are comfortable at rest.

A patient with cardiac disease resulting in marked limitation of physical activity is classified as a NYHA class III. Less than ordinary activity causes fatigue, palpitation, dyspnea or anginal pain. They are comfortable at rest.

A patient with cardiac disease resulting in inability to carry on any physical activity without discomfort is classified as a NYHA class IV. Symptoms of cardiac insufficiency or of the anginal syndrome may be present even at rest. If any physical activity is undertaken, discomfort is increased.

The term "detecting" or "determining" as used above includes qualitative and/or quantitative detection (measuring levels) with or without reference to a control. Typically IGFBP2 concentrations may be measured for example by capillary electrophoresis-mass spectroscopy technique (CE-MS), other mass spectrometry techniques or ELISA performed on the sample.

Preferably, the invention relates to a method for establishing if a heat patient is susceptible to be hospitalized and/or rehospitalized comprising a step a) consisting of measuring IGFBP2 concentration in a sample obtained from said heart failure patient. Preferably, the method of the invention further comprises a step of comparing the concentration of IGFBP2 obtained in step a) to a threshold level.

The "control" may be a healthy subject, i.e. a subject who does not suffer from any heart failure. The control may also be a subject suffering from heart failure. Preferably, said control is a healthy subject.

Detection of IGFBP2 concentration in the sample may also be performed by measuring the level of IGFBP2 protein. In the present application, the "level of IGFBP2 protein" means the quantity or concentration of said IGFBP2 protein. In another embodiment, the "level of IGFBP2" means the level of IGFBP2 fragments.

Such methods comprise contacting a sample with a binding partner capable of selectively interacting with IGFBP2 protein peptides present in the sample. The binding partner is generally an antibody that may be polyclonal or monoclonal, preferably monoclonal.

The presence of the protein can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, capillary electrophoresis-mass spectroscopy technique (CE-MS). etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound protein in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

More particularly, an ELISA method can be used, wherein the wells of a microtiter plate are coated with a set of antibodies against the proteins to be tested. A sample containing or suspected of containing the marker protein is then added to the coated wells. After a period of incubation sufficient to allow the formation of antibody-antigen complexes, the plate(s) can be washed to remove unbound moieties and a detectably labeled secondary binding molecule is added. The secondary binding molecule is allowed to react with any captured sample marker protein, the plate is washed and the presence of the secondary binding molecule is detected using methods well known in the art.

Methods of the invention may comprise a step consisting of comparing IGFBP2 protein and fragments concentration in circulating cells with a control value. As used herein, "concentration of IGFBP2" refers to an amount or a concentration of a transcription product, for instance the protein IGFBP2. Typically, a level of a protein can be expressed as nanograms per microgram of tissue or nanograms per milliliter of a culture medium, for example. Alternatively, relative units can be employed to describe a concentration. In a particular embodiment, "concentration of IGFBP2" may refer to fragments of IGBP2. Thus, in a particular embodiment, fragments of IGFBP2 may also be measured.

Figure 2:
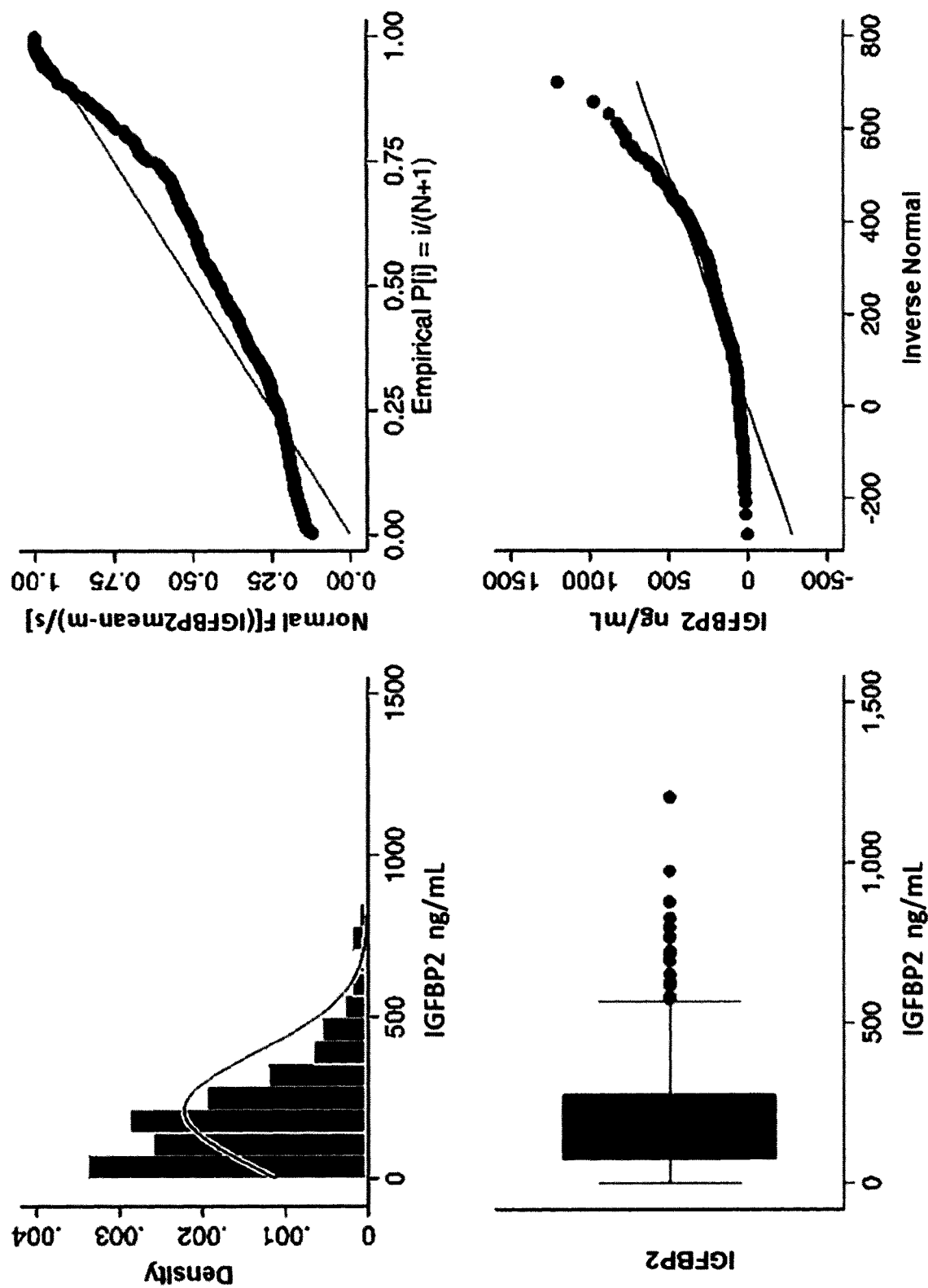
Figure 3:
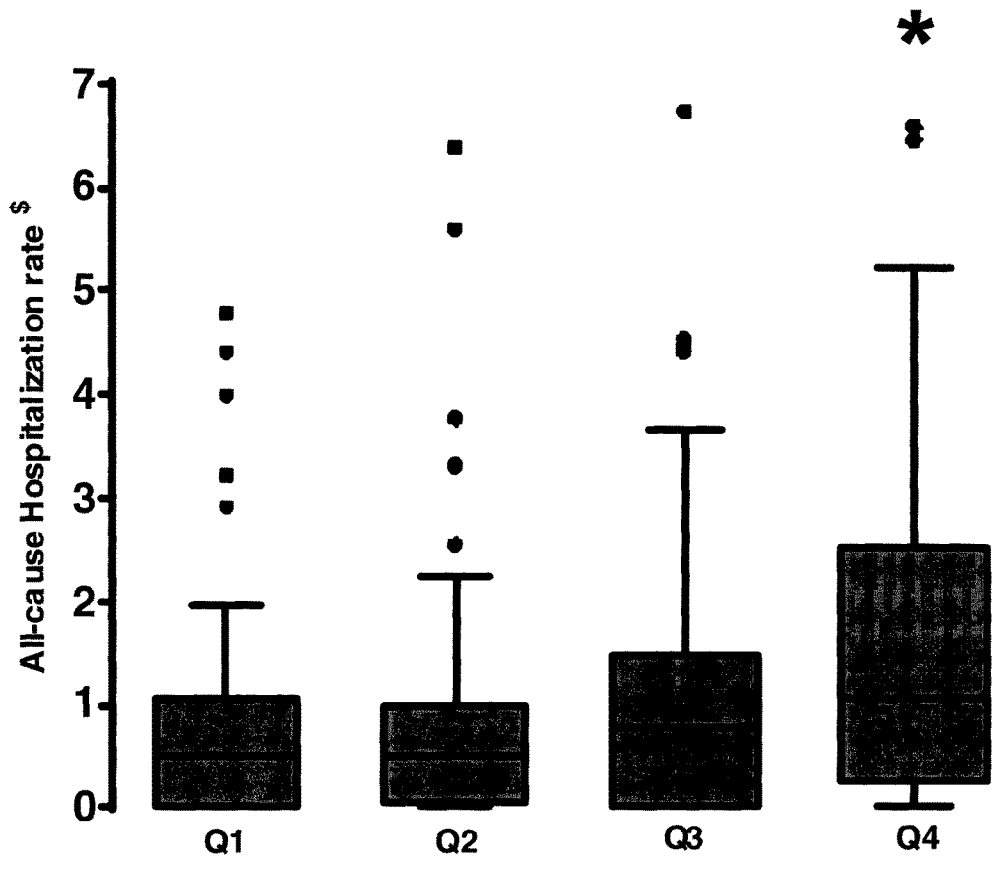
Figure 4:
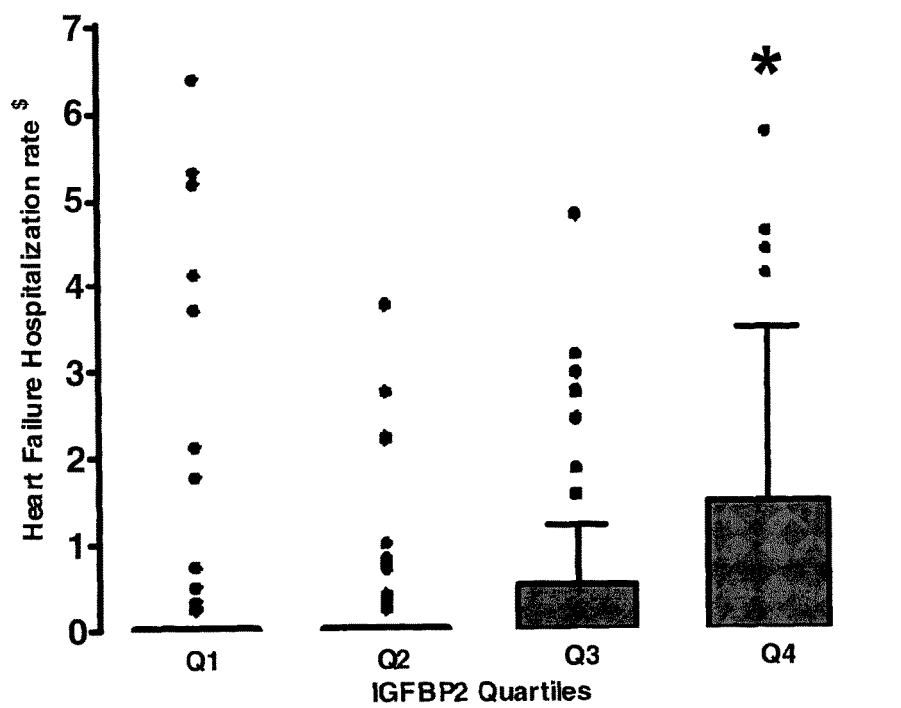

The inventors have established that the risk of hospitalization and/or rehospitalization of a patient is associated with the concentration of IGFBP2 protein in plasma. Thus, the proportion of patients hospitalized or rehospitalized for heart failure disease is higher when IGFBP2 protein plasma is higher than 171 ng/ml (the median concentration value of IGFBP2 protein plasma in the cohort, (FIG. 1, FIG. 2, table 4). Annual rate of hospitalisation for heart failure and other causes is positively correlated to IGFBP2 protein plasma concentration (FIG. 3 and FIG. 4, respectively). The risk of hospitalization and or rehospitalisation for a patient is proportional to the concentration of IGFBP2 protein in plasma. Thus, per each increase of 100 ng/ml of IGFBP2 protein the hospitalization/rehospitalization rate is increase by 20%. In another word, all 100 ng/ml more than the threshold value of 171 ng/ml (the median concentration value of IGFBP2 in the cohort), a patient has a 20% chance more of being rehospitalized for a heart failure and all-cause (see table 3, table 4). In still another word and for explanation, a patient with a concentration of IGFBP2=threshold value +100 ng/ml has 20% chance more of being rehospitalized for an heart failure. A patient with a concentration of IGFBP2=threshold value +200 ng/ml has 40% chance more of being rehospitalized for an heart failure. A patient with a concentration of IGFBP2=threshold value +300 ng/ml has 60% chance more of being rehospitalized for an heart failure.

Typically, a "threshold value", "threshold level" or "cut-off value" can be determined experimentally, empirically, or theoretically. A threshold value can also be arbitrarily selected based upon the existing experimental and/or clinical conditions, as would be recognized by a person of ordinary skilled in the art. Preferably, the person skilled in the art may compare the concentration of IGFBP2 obtained according to the method of the invention with a defined threshold value.

Preferably, said threshold value is the mean concentration of IGFBP2 of a population of healthy individuals. As used herein, the term "healthy individual" denotes a human which is known to be healthy, i.e. which does not suffer from heart failure, has never been subjected to such chronic heart failure, and does not need any medical care.

Preferably, said threshold value is the mean concentration of IGFBP2 of a population of sick individuals. As used herein, the term "sick individual" denotes a human which is known to be sick, i.e. which suffers from heart failure at any stage of heart failure as according to the NYHA heart failure classification.

Typically, the skilled person in the art may determine the concentration of IGFBP2 in a biological sample, preferably plasma or urine, of 100 individuals known to be healthy or sick. The mean value of the obtained concentrations is then determined, according to well known statistical analysis, so as to obtain the mean concentration of IGFBP2. Said value is then considered as being normal and thus constitute a threshold value. By comparing the concentrations of IGFBP2 to this threshold value, the physician is then able to establish if a heart failure patient should be rehospitalized. Indeed, by comparing the concentrations of IGFBP2 obtained in a biological sample, preferably plasma or urine, of a given subject to a threshold value, one can easily determine whether said subject suffers from heart failure or not or can easily determine the stage of the heart failure according to the NYHA heart failure classification.

Accordingly, the physician would be able to adapt and optimize appropriate medical care of a subject in a critical and life-threatening condition suffering from heart failure. The determination of said prognosis is highly appropriate for follow-up care and clinical decision making.

Therefore, the invention is drawn to a method for establishing if a heart failure patient is susceptible to be rehospitalized comprising the following steps:
 a) determining the concentration of IGFBP2 in a sample obtained from said heart failure patient;
 b) determining the mean concentration of IGFBP2 in a biological sample of a population of healthy or sick individuals, preferably 100 healthy individuals; and
 c) a step of comparing the concentration of IGFBP2 obtained of a) to the mean concentration of IGFBP2 obtained in b).

Yet another object of the invention relates to a kit for performing a method of the invention, said kit comprising means for measuring the concentration of IGFBP2 in a sample obtained from a heart failure patient.

The kit may include an antibody, or a set of antibodies as above described. In a particular embodiment, the antibody or set of antibodies are labelled as above described. The kit may also contain other suitably packaged reagents and materials needed for the particular detection protocol, including solid-phase matrices, if applicable, and standards. The kit may also contain one or more means for the detection of a further biomarker.

A further object of the invention relates to a method for establishing if a heart failure patient is susceptible to be hospitalized and/or rehospitalized wherein said method further comprises the steps of:
 (i) measuring the concentration of IGFBP2 in a sample obtained from said heart failure patient,
 (ii) comparing the concentration of IGFBP2 measured in step (i) to a threshold value derived from the concentration of IGFBP2 in samples from healthy patients wherein when the concentration of IGFBP2 in said sample is higher than the threshold then the patient is susceptible to hospitalized or rehospitalized.

A further object of the invention relates to the use of IGFBP2 as a biomarker for hospitalization and/or rehospitalisation of a patient after an heart failure.

The invention will be further illustrated by the following figures and examples. However, these examples and figures should not be interpreted in any way as limiting the scope of the present invention.

FIGURES

FIG. 1: The Atlanta Cardiomyopathy Consortium: Study Design

FIG. 2: IGFBP2 descriptive statistics. IGFBP2 Mean±SD: 211±180 ng/mL, Median (IQR): 172 [76, 274] ng/mL. Distribution of IGFBP2: lognormal test (Shapiro-Wilk W test for lognormal data: P=0.90)

FIG. 3: Box plot of all-cause of hospitalization rate by quartiles of IGFBP2.

FIG. 4: Box plot of heart failure hospitalization rate by quartiles of IGFBP2.

TABLE 1

| Patients Characteristics (N = 306) Clinical Characteristics: |
|---|
| Age: 57 ± 12 years |
| Sex: 196 male (64.0%), 110 female (36.0%) |
| Race: 158 white (51.6%), 138 black (45.1%), 10 other (3.3%) |
| Etiology: 125 ischemic (40.8%), 181 nonischemic (59.2%) |
| LV Ejection Fraction: 37 [25, 50] % |
| NYHA class: 214 I-II (69.9%); 92 III-IV (30.1%) |
| Diabetes Mellitus: 102 (33.3%) |
| Systolic Blood Pressure: 113 ± 20 mmHg |
| BNP: 210 [70, 662] ng/mL (in 240 participants) |
| Creatinine: 1.2 [1.0, 1.5] mg/dL |
| Blood Urea Nitrogen: 18 [13, 26] mg/dL |
| Sodium: 138.4 ± 2.9 mEq/dL |
| Hemoglobin: 13.2 ± 1.8 g/dL |
| β-Blockers: 279 (91.2%) |
| ACEI or ARB: 239 (78.1%) |
| Aldosterone antagonists: 134 (43.8%) |
| ICD ± CRT Device: 194 (64.5%) |
| Echocardiographic PASP in 212 pts: 41 ± 15 mmHg |

ABBREVIATIONS

LV, left ventricular; NYHA, New-York heart association; BNP, brain natriuretic peptide; ACEI, angiotensin-converting enzyme inhibitor; ARB, angiotensin receptor blocker; ICD, implantable cardiac defibrillator; CRT, cardiac resynchronization therapy; PASP, pulmonary arterial systolic pressure.

Normal continuous variables are expressed as mean±standard deviation.

Non-normal variables are expressed as median and [interquartile range].

Categorical variables are expressed as number of occurrence and (percentage).

TABLE 2

Correlation of IGFBP2 with Clinical Characteristics

| Characteristic | Spearman's rho | P value |
|---|---|---|
| Age | 0.107 | 0.062 |
| Sex (Male = 0; Female = 1) | −0.073 | 0.20 |
| Race (White = 1) | −0.078 | 0.17 |
| Etiology (Ischemic = 1) | 0.078 | 0.17 |
| LV Ejection Fraction | −0.089 | 0.12 |
| NYHA Class | 0.097 | 0.095 |
| Diabetes Mellitus | 0.076 | 0.19 |
| Systolic Blood Pressure | −0.104 | 0.071 |
| BNP (in 240 pts) | 0.319 | <0.0001 |
| Creatinine | 0.318 | <0.0001 |
| Blood Urea Nitrogen | 0.312 | <0.0001 |
| Sodium | −0.018 | 0.76 |
| Hemoglobin | −0.206 | 0.0005 |
| β-Blockers | 0.044 | 0.44 |
| ACEI or ARB | −0.167 | 0.0034 |
| Aldosterone antagonists | −0.009 | 0.87 |
| ICD/CRT Device | 0.009 | 0.87 |
| Echo PASP (in 212 pts) | 0.220 | 0.0013 |

LV, left ventricular; NYHA, New-York heart association; BNP, brain natriuretic peptide; ACEI, angiotensin-converting enzyme inhibitor; ARB, angiotensin receptor blocker; ICD, implantable cardiac defibrillator; CRT, cardiac resynchronization therapy; PASP, pulmonary arterial systolic pressure.

TABLE 3

Outcomes
Follow-up: median, 3.1 [1.9, 3.9] years; mean, 2.8 ± 1.1 years
52 major clinical events: 42 deaths; 5 left ventricular assist device (LVAD) implantation; 5 urgent cardiac transplantation.
765 all-cause admissions; 278 admissions (36.3% of all admissions) for HF.
Association of IGFBP2 (continuous variable) with outcomes (N = 303)

| Univariate analysis | | |
|---|---|---|
| Association with major clinical events (Cox regression): HR per 100 ng/mL | 1.22 (95% CI: 1.09 to 1.36) | P < 0.001 |
| Association with all-cause admissions (Poisson process, negative binomial regression): IRR per 100 ng/mL | 1.12 (95% CI: 1.03 to 1.22) | P = 0.007 |
| Mulivariate analysis* | | |
| Association with major clinical events (Cox regression): HR per 100 ng/mL | 1.23 (95% CI: 1.06 to 1.43) | P = 0.005 |
| Association with HF admissions (Poisson process, negative binomial regression): IRR per 100 ng/mL | 1.20 (95% CI: 1.00 to 1.44); | P = 0.05 |

*Adjustment model: age, gender, race, etiology, NYHA class, systolic blood pressure, sodium, blood urea nitrogen (stronger than creatinine and collinear), LVEF, hemoglobin, treatment (beta-blockers, ACEI or ARB, aldosterone antagonists, implantable device).
HR: hazard ratio; IRR, incident rate ratio.

TABLE 4

Hospitalization and re-hospitalization rates with IGFBP2 concentration below and above the threshold value.

Outcomes according to high IGFBP2 and low IGFBP2 (dichotomized status) (N = 303)

| Outcome | Low IGFBP2 IGFBP2 < 172 ng/ml | High IGFBP2 IGFBP2 > 172 ng/ml | Incident Rate Ratio (95% CI) | P value |
|---|---|---|---|---|
| Resource utilisation (per 100-person-y) | | | | |
| All-cause hospitalizations | 72.8 | 104.2 | 1.43 (1.24-1.65) | <0.0001 |
| Heart failure hospitalizations | 21.8 | 43.1 | 1.98 (1.54-2.55) | <0.0001 |
| Total all-cause hospitalized days | 274 | 566 | 1.94 (1.81-2.07) | <0.0001 |
| Total heart failure-related hospitalized days | 175 | 346 | 1.97 (1.81-2.15) | <0.0001 |
| All-cause re-hospitalizations | 111 | 151 | 1.37 (1.15-1.63) | <0.0001 |
| Patients distribution | | | | |
| All-cause Hospitalized patients 73% (N = 221) | 48% (106) | 52% (115) | | =0.710 |
| All-cause Re-Hospitalized patients 51% (N = 155) | 44% (69) | 55% (86) | | =0.311 |
| HF hospitalized patients 31% (N = 95) | 36% (34) | 64% (61) | | =0.021 |
| HF re-hospitalized patients 18% (N = 54) | 31% (17) | 68% (37) | | =0.018 |

EXAMPLES

Material & Methods

Patient Population

The Atlanta Cardiomyopathy Consortium is a prospective cohort study enrolling outpatients with HF from three university-affiliated hospitals in the greater metropolitan Atlanta area (FIG. 1). Inclusion criteria included age >18 years, able to understand and sign written informed consent and participate, and a diagnosis of HF with either reduced or preserved ejection fraction. The diagnosis of HF with preserved ejection fraction required, in addition to clinical diagnosis of HF, elevated B-type natriuretic peptide level >200 pg/dl and/or an echocardiogram evidence of diastolic dysfunction. [Paulus W J et al., 2007] Exclusion criteria included congenital heart disease, previous heart transplantation or awaiting transplant, known cardiac infiltrative disease (e.g., amyloidosis), previous other solid organ transplantation, and end-stage HF requiring outpatient continuous inotrope infusion.

Study Procedures

All patients undergo past history surveys, history and physical examination, electrocardiogram, 6-minute walk test, several questionnaires, and collection of blood and urine samples at baseline. Race is self-reported. Every six months, the patients are contacted to assess medication changes, procedures, new diagnoses, and hospitalizations. Mortality data are collected through medical record review, information from family members, and Social Security Death Index query. Hospitalization data are obtained from electronic health records review, outpatient notes from any specialty encounter for any admission to an outside hospital, and direct patient inquiry during follow-up. The Institutional Review Board has approved the study. Informed consent was obtained from all patients prior to enrollment.

Outcomes

Clinical event was defined as a composite of death, heart transplantation, or left ventricular assist device placement. Resource utilization was assessed as emergency department visits, all-cause and HF hospitalizations, and total number of days hospitalized per 100 person-year follow-up.

Blood Sample Collection

All subjects were venesected after 15 min bed-rest, and peripheral venous blood was drawn into sodium/EDTA tubes. After centrifugation at 1500 g at 4° C. for 15 min, plasma was separated, aliquoted and stored at −80° C. until assayed.

Immune Methods

IGFBP-2 enzyme-linked immunosorbent assay. The R&D DuoSet ELISA development kit (sandwich ELISA; no. DY674; R&D Systems, Inc., Minneapolis, Minn.) was used to measure human IGFBP-2 as per the manufacturer's specifications.

Results

Study Participants

The baseline patient characteristics are presented in Table 1. Mean age of patients was 57±12 years (range 25-87 years); 36% female, and 45.1% black. The majority of patients had HF with reduced ejection fraction.

Correlation Analysis

IGFBP2 plasma levels were not associated to age, sex, race, etiology, left ventricular ejection fraction, NYHA class, diabetes mellitus, systolic blood pressure, sodium, b-blockers, aldosterone antagonist ICD/CRT device. IGFBP2 levels were positively associated with BNP, Creatinine, blood urea nitrogen, echocardiographic PASP and negatively associated with hemoglobin, ACEI and ARB drugs prescription (see table 2).

Outcomes

During a mean follow-up of 2.8±1.1 years (total: 857 patient-years), 42 patients died, 5 underwent transplantation, and 5 received ventricular assist devices, for a total clinical event rate of 12% and annualized event rate of 6%. HF hospitalizations and number of days hospitalized as well as lower all-cause and HF-specific emergency department visits were recorded. Patients were subject to 765 all-cause admissions; 278 admissions (36.3% of all admissions) for HF. Although the distribution of IGFBP2 is lognormal, the form of association with major clinical events and hospitalizations is linear (evaluated with both fractional polynomials and restricted cubic splines), so no transformation was needed for modeling of outcomes (FIG. 2). Patients with IGFBP2 protein plasma concentration higher than median value (172 ng/ml) are significantly more hospitalized or rehospitalized for HF (Table 4). Analyse of hospitalization rate of patients stratified into quartiles according to their IGFBP2 protein plasma concentration demonstrates that there is a positive trend between the IGBP2 concentration and the patient hospitalisation rate and that patient in the highest quartile have a significantly higher hospitalisation rate for all-cause and heart failure than patients in the first or second quartiles, FIG. 3 and FIG. 4, respectively.

Univariate analysis revealed an association of IGFBP2 with major clinical events (HR=1.22 per 100 ng/mL; 95% CI [1.09-1.36]; P<0.001), and the rate of all-cause admissions (IRR=1.12 per 100 ng/mL (95% CI [1.03-1.22]; P=0.007). The adjusted model in the multivariate analysis indeed showed that the risk of major clinical events increased with the IGFBP2 level (HR=1.23 per 100 ng/mL; 95% CI [1.06-1.43]; P=0.005); and the rate of admission for heart failure increased with the IGFBP2 level (IRR: 1.20 per 100 ng/mL; 95% CI [1.00 to 1.44]; P=0.05) (see table 3). Thus, IGFBP2 is a potent prognostic marker of rehospitalization.

REFERENCES

Throughout this application, various references describe the state of the art to which this invention pertains. The disclosures of these references are hereby incorporated by reference into the present disclosure.

Delahaye, F., Roth, O., Aupetit, J. F. & de Gevigney, G. [Epidemiology and prognosis of cardiac insufficiency]. Arch Mal Coeur Vaiss 94, 1393-1403 (2001).

Mischak, H. et al. Comprehensive human urine standards for comparability and standardization in clinical proteome analysis. Proteomics Clin Appl 4, 464-478, doi:10.1002/prca.200900189 (2010).

Paulus W J, Tschope C, Sanderson J E, Rusconi C, Flachskampf F A, Rademakers F E, et al. How to diagnose diastolic heart failure: a consensus statement on the diagnosis of heart failure with normal left ventricular ejection fraction by the Heart Failure and Echocardiography Associations of the European Society of Cardiology. European Heart Journal. 2007; 28:2539-50.

Phillips K, M A Park, L H Quarrie, M Boutinaud, J D Lochrie, D J Flint, G J Allan, J Beattie. Hormonal control of IGF-binding protein (IGFBP)-5 and IGFBP-2 secretion during differentiation of the HC11 mouse mammary epithelial cell line. Journal of molecular endocrinology, 31:197-208 (2003).

The invention claimed is:

1. A method for avoiding rehospitalization and treating a heart failure patient with a clinical diagnosis of heart failure, wherein said method comprises
obtaining a biological sample selected from the group consisting of blood, plasma, and urine from said patient,
measuring the concentration of IGFBP2 in said sample obtained from said patient with the clinical diagnosis of heart failure, and
comparing the concentration of IGFBP2 measured in said measuring step to a threshold value derived from the concentration of IGFBP2 in blood samples taken from a group of patients wherein each of the patients in the group has one or more stages of heart failure selected from the group consisting of stage I, stage II, stage III and stage IV, according to the New York Heart Association (NYHA) heart failure classification system,
rehospitalizing said patient with the clinical diagnosis of heart failure if the measured concentration exceeds the threshold value, and
administering to said patient with the clinical diagnosis of heart failure at least one treatment selected from the group consisting of an effective amount of a beta-blocker, an effective amount of an angiotensin-converting enzyme inhibitor, an effective amount of an angiotensin receptor blocker, an effective amount of an aldosterone antagonist, an implantable cardiac defibrillator, a cardiac resynchronization therapy, an implantable left ventricular assistive device and a heart transplant,
wherein the clinical diagnosis of heart failure is a diagnosis of heart failure with either reduced or preserved ejection fraction.

2. The method according to claim 1, wherein said sample is plasma.

3. The method according to claim 1, wherein the concentration of IGFBP2 is measured by quantifying the level of IGFBP2 protein in the sample.

4. The method according to claim 3, wherein the quantification of the level of IGFBP2 protein is performed by using a set of antibodies directed against IGFBP2.

5. The method according to claim 3, wherein the quantification of the level of IGFBP2 protein is performed by ELISA.

6. The method according to claim 3, wherein the quantification of the level of IGFBP2 protein is performed by capillary electrophoresis-mass spectroscopy technique (CE-MS).

7. A method for treating a heart failure patient who has been previously hospitalized for heart failure, comprising
obtaining a blood sample said heart failure patient with diastolic dysfunction, measuring by ELISA the concentration of IGFBP2 in said blood sample obtained from said heart failure patient,
comparing the concentration of IGFBP2 measured in said measuring step to a threshold value derived from the concentration of IGFBP2 in blood samples taken from a group of patients wherein each of the patients in the group has stage IV heart failure according to the New York Heart Association (NYHA) heart failure classification system,
readmitting said heart failure patient for further hospitalization if said concentration of IGFBP2 measured in said measuring step exceeds the threshold value, and
administering to said heart failure patient at least one treatment selected from the group consisting of an effective amount of a beta-blocker, an effective amount of an angiotensin-converting enzyme inhibitor, an effective amount of an angiotensin receptor blocker, an effective amount of an aldosterone antagonist, an implantable cardiac defibrillator, a cardiac resynchronization therapy, an implantable left ventricular assistive device and a heart transplant.

8. The method according to claim 1 wherein said sample is urine.

9. The method according to claim 1 wherein the group of patient used for deriving said threshold value is derived from a group of patients with stage I heart failure.

10. The method according to claim 1 wherein the group of patient used for deriving said threshold value is derived from a group of patients with stage II heart failure.

11. The method according to claim 1 wherein the group of patient used for deriving said threshold value is derived from a group of patients with stage III heart failure.

12. The method according to claim 1 wherein the group of patient used for deriving said threshold value is derived from a group of patients with stage IV heart failure.

13. The method of claim 1, wherein the clinical diagnosis of heart failure includes a diagnosis of one or more of chronic heart failure, acute heart failure, myocardial infarction, unstable angina, diastolic dysfunction, systolic dysfunction and diabetic cardiomyopathy.

* * * * *